(12) United States Patent
Buisman

(10) Patent No.: US 8,912,895 B2
(45) Date of Patent: Dec. 16, 2014

(54) MEDICAL DEVICE HAVING A REMINDER FUNCTION

(75) Inventor: Harm Jacob Buisman, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 361 days.

(21) Appl. No.: 13/375,791

(22) PCT Filed: Jun. 7, 2010

(86) PCT No.: PCT/IB2010/052508
§ 371 (c)(1),
(2), (4) Date: Dec. 2, 2011

(87) PCT Pub. No.: WO2010/143115
PCT Pub. Date: Dec. 16, 2010

(65) Prior Publication Data
US 2012/0075085 A1   Mar. 29, 2012

(30) Foreign Application Priority Data

Jun. 12, 2009  (EP) ..................................... 09162617

(51) Int. Cl.
*G08B 1/00* (2006.01)
*G04F 8/00* (2006.01)
*G06F 19/00* (2011.01)
*A61J 7/04* (2006.01)
*A61B 5/00* (2006.01)

(52) U.S. Cl.
CPC .............. *A61B 5/00* (2013.01); *G06F 19/3418* (2013.01); *A61J 7/0472* (2013.01); *G06F 19/363* (2013.01); *A61J 2200/30* (2013.01)
USPC .......... 340/309.7; 340/309.16; 368/9; 368/10

(58) Field of Classification Search
None
See application file for complete search history.

(56) References Cited

U.S. PATENT DOCUMENTS

| 6,018,289 | A  | * | 1/2000  | Sekura et al. ............... 340/309.4 |
| 6,560,165 | B1 |   | 5/2003  | Barker |
| 7,607,431 | B1 |   | 10/2009 | Cruitt et al. |
| 7,953,613 | B2 | * | 5/2011  | Gizewski .......................... 705/3 |
| 2002/0097156 | A1 |   | 7/2002 | Broas |
| 2006/0123053 | A1 | * | 6/2006 | Scannell, Jr. ................ 707/104.1 |
| 2008/0162352 | A1 | * | 7/2008 | Gizewski ......................... 705/50 |
| 2011/0273280 | A1 | * | 11/2011 | Chang et al. ................ 340/309.7 |
| 2012/0293328 | A1 | * | 11/2012 | Blomquist ..................... 340/540 |
| 2013/0183749 | A1 | * | 7/2013 | Aamodt et al. ............. 435/287.1 |

* cited by examiner

Primary Examiner — Julie Lieu

(57) ABSTRACT

There is provided a medical device having a reminder function, the medical device comprising a reminder generator for issuing a reminder to a user to perform a predetermined action with the medical device; and a controller for selecting the reminder from a plurality of available reminders and for controlling the reminder generator to issue the selected reminder in accordance with a reminding schedule; wherein the controller is configured to maintain a measure of the effectiveness of each of said available reminders and to select the reminder from the plurality of available reminders based on said measures.

17 Claims, 2 Drawing Sheets

MEDICAL DEVICE HAVING A REMINDER FUNCTION

TECHNICAL FIELD OF THE INVENTION

The invention relates to a medical device, such as a monitoring device or a medicament dispensing device, and a method of operating a medical device, and in particular to a medical device having a reminder function.

BACKGROUND TO THE INVENTION

In the healthcare sector, many devices and systems are being developed that allow a patient to carry out monitoring of various conditions in their home or work environment or while on the move, without requiring the direct supervision of a healthcare professional.

In these systems, the patient can be provided with a monitoring device, such as a blood sugar meter, a blood INR meter, a heart rate monitor, a blood pressure meter, and so on, that the patient uses to take regular or frequent measurements of some physiological parameter(s). The monitoring device can then provide the results of the measurement to a computer terminal in the patient's home, and the computer terminal can forward the results to a remote station (such as a healthcare professional's computer terminal), where the results can be collated and reviewed by a healthcare professional. The healthcare professional can contact the patient if the results are unsatisfactory or if the patient needs to change their treatment regimen.

However, this type of system is only effective if the patient uses the monitoring device at the required intervals.

A similar problem exists with home medicament dispensing devices that regularly or frequently dispense a medicament to a patient. The medication therapies can only be effective if the patient takes their medicament at the appropriate time.

Therefore, there is a need for a medical device having a reminder function that motivates the patient or user to use the medical device at the appropriate time.

SUMMARY OF THE INVENTION

According to a first aspect of the invention, there is provided a medical device comprising medical device having a reminder function, the medical device comprising a reminder generator for issuing a reminder to a user to perform a predetermined action with the medical device; and a controller for selecting the reminder from a plurality of available reminders and for controlling the reminder generator to issue the selected reminder in accordance with a reminding schedule; wherein the controller is configured to maintain a measure of the effectiveness of each of said available reminders and to select the reminder from the plurality of available reminders based on said measures.

According to a second aspect of the invention, there is provided a method of operating a medical device, the method comprising determining that a reminder should be issued to a user of the medical device to remind the user to perform a predetermined action with the medical device; selecting a reminder from a plurality of available reminders, the selection of the reminder being based on measures of the effectiveness of each of said reminders in the plurality; and issuing the selected reminder to the user.

According to a third aspect of the invention, there is provided a computer program product comprising computer readable code embodied therein, wherein the computer readable code is configured to cause a computer or processor to perform the method described above.

BRIEF DESCRIPTION OF THE DRAWINGS

Preferred embodiments of the invention will now be described, by way of example only, with reference to the following drawings, in which.

DETAILED DESCRIPTION OF THE PREFERRED EMBODIMENTS

Figure 1:
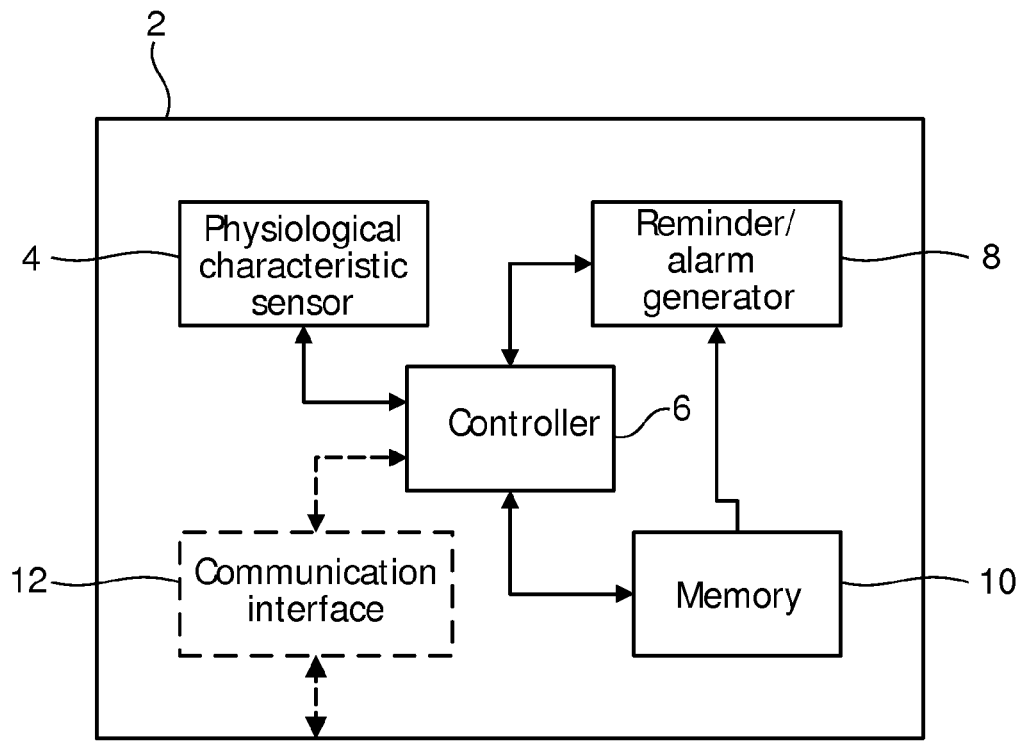
FIG. 1 is a block diagram of a medical monitoring device according to a first embodiment of the invention.

A first specific embodiment of the invention, in the form of a medical monitoring device, is shown in FIG. 1.

The medical monitoring device 2 comprises a physiological characteristic sensor 4 for taking a measurement or measurements of a physiological characteristic of the user of the device 2. The physiological characteristic sensor 4 is connected to a controller 6 that controls the operation of the medical monitoring device 2.

The specific form of the sensor 4 will depend on the use to which the device 2 is to be put. For example, if the device 2 is to be used to aid in the treatment of diabetes, the physiological characteristic sensor 4 may be a sensor for measuring blood sugar levels. It will be appreciated that any other type of physiological characteristic sensor 4 can be used in the medical monitoring device 2, including a weight sensor, a heart rate monitor, blood pressure monitor, a blood INR level sensor, an SpO2 meter, an electrocardiogram (ECG), an electroencephalogram (EEG) or an electromyogram (EMG).

Of course, it will be appreciated that the device 2 may be used for the treatment of a variety of conditions, so the device 2 may comprise more than one type of physiological characteristic sensor 4.

The medical monitoring device 2 also comprises a reminder/alarm generator 8 for generating and issuing a reminder or an alarm to the user of the device 2. The reminder or alarm is generated to prompt the user of the device 2 to take a measurement using the physiological characteristic sensor 4. The reminder/alarm generator 8 can generate a variety of different reminders or alarms, for example using one or more modalities (for example using sounds such as beeps, music clips or voice messages; visual elements such as lights, images, text-based messages or video, vibration and/or smells) and with different parameters for each modality (for example volume, intensity, frequency, duration).

The data for these specific reminders or alarms can be stored in a memory 10 that is accessible by the reminder/alarm generator 8 and that is also connected to the controller 6. As suggested above, this data can comprise samples or computer files for a selection of audible alarms having different intensities and frequencies, pre-recorded voice or video messages (for example from a healthcare provider or a relative or friend of the user), images or text-based messages.

The medical monitoring device 2 determines, or is provided with, a reminder schedule that specifies when the controller 6 should control the reminder/alarm generator 8 to issue selected reminders to the user of the device 2. This reminder schedule can be stored in the memory 10. The reminder schedule can be determined from a measurement schedule that indicates a specific time or time window in which the user should take a measurement using the device 2. This measurement schedule can also be stored in the memory 10.

The memory 10 can also store the result of any measurement taken by the device 2.

The medical monitoring device 2 may also comprise a communication interface 12 that allows the medical monitoring device 2 to transmit information to and receive information from other devices. For example, the results from the measurements made using the physiological characteristic sensor 4 can be transmitted from the device 2 to the computer of a healthcare provider for review. The communication interface 12 may also be used to receive a new reminder schedule or updates to the reminder schedule from a healthcare provider or updates or changes to the algorithm used by the controller 6 to select a reminder or alarm to issue, or to transmit the reminder schedule to another device, such as a mobile phone or personal computer.

In accordance with the invention, in order to improve the user's compliance in taking measurements with the medical monitoring device 2, the controller 6 determines and maintains in the memory 10 a measure of the effectiveness of different reminders (including the particular parameters used) that have been used to prompt the user to take a measurement using the device 2. Then, when a reminder needs to be issued, the controller 6 can select a reminder for use based on the measures of the effectiveness.

The controller 6 can select the reminder to use at the time that a reminder needs to be issued (i.e. dynamically), or the controller 6 can specify the reminder to be issued at a particular time when the reminding schedule is being compiled.

In a preferred embodiment, the measure of the effectiveness of a particular reminder (or a reminding pattern comprising a number of reminders that are issued before the user takes a measurement using the device 2) is based on the average time difference between a planned measurement (i.e. when the reminder is issued) and the actual time that the user takes the measurement.

When a reminder is issued by the reminder/alarm generator 8, the controller 6 notes the details of the reminder (i.e. the modality/modalities of the reminder and the parameter values used), updates a previous value for the effectiveness of that reminder (previous_effectiveness) and stores this updated value in the memory 10, along with an indication of the number of times that that particular reminder has been used. An exemplary equation for determining the updated effectiveness is shown in equation (1) below:

$$\text{updated\_effectiveness} = \frac{(\text{nr\_times\_used\_before} + 1)}{\left(\text{new\_time\_lapse} + \frac{\text{nr\_times\_used\_before}}{\text{previous\_effectiveness}}\right)} \quad (1)$$

By maintaining and updating a measure of the effectiveness of each different reminder, it will be appreciated that it is possible for the controller 6 to learn which reminder or reminders are most and/or least effective for a particular user of the device 2.

Figure 2:
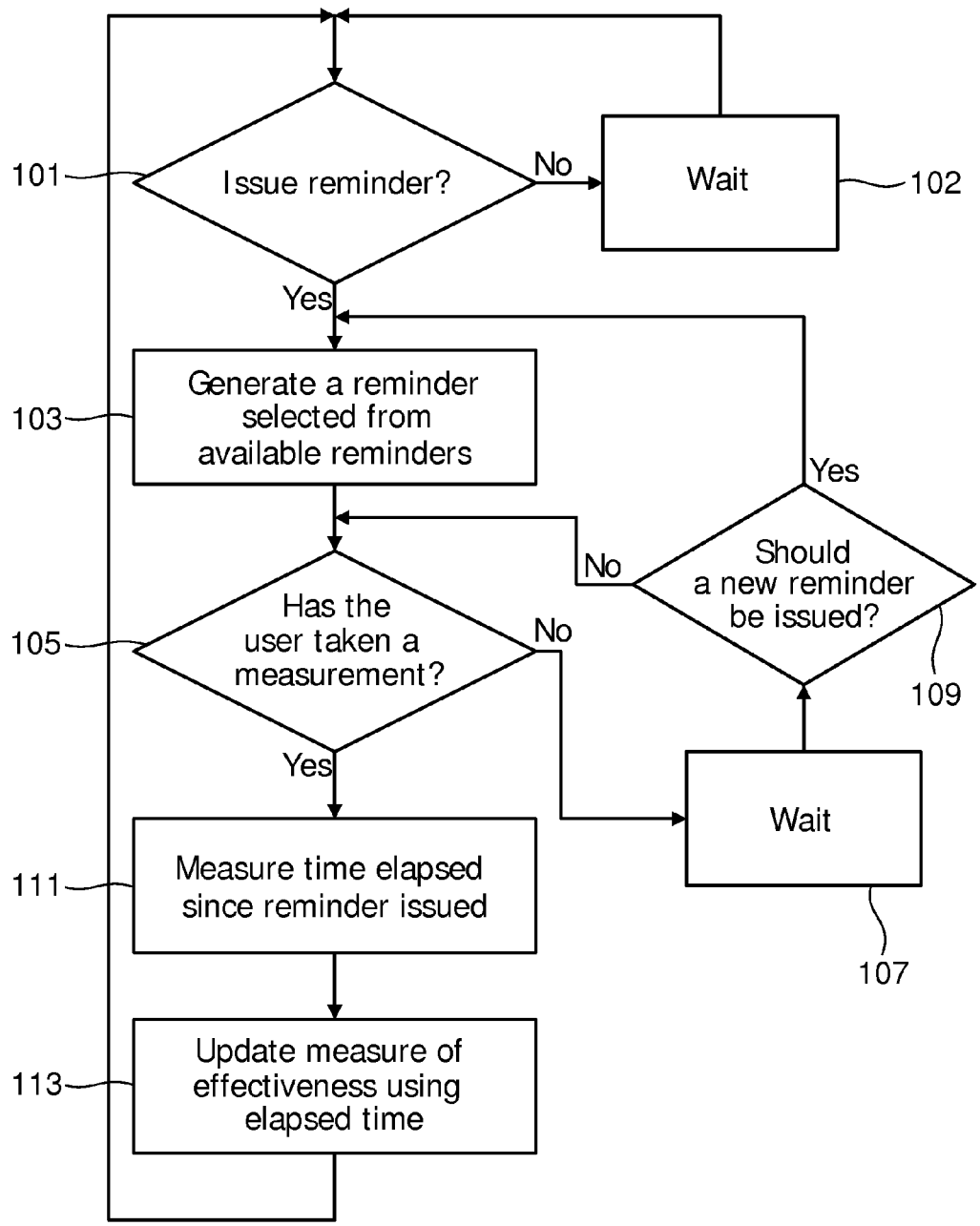
FIG. 2 is a flow chart illustrating the method of operating the medical monitoring device according to the first embodiment of the invention.

A method of operating the medical monitoring device 2 is shown in FIG. 2.

In step 101, it is determined whether a reminder should be issued. As described above, the controller 6 can determine this from the reminder schedule. If it is not time to issue a reminder, the controller 6 waits for a predetermined time period (step 102) before returning to step 101.

If a reminder should be issued, the method moves to step 103 in which a reminder is selected from the available reminders stored in the memory 10 and is generated by the reminder/alarm generator 8.

As indicated above, the controller 6 can select the reminder modality and parameter values when it is determined that a reminder should be issued, or the reminder modality and parameter values can be specified by the controller 6 when the reminder schedule is being compiled.

In this step, the controller 6 can operate in either a training mode or a normal mode. Broadly speaking, the training mode allows the controller 6 to learn which reminder or reminders are most/least effective for the user of the device 2, while the normal mode allows the controller 6 to use the reminder or reminders that have been found to be most effective for the user of the device 2.

In the training mode, the controller 6 is programmed so that it does not automatically select the most effective reminder or reminders for use, but selects the reminder from all of the available reminders. The reminder could be selected randomly, or the selection could be made from those reminders that have been used least often (i.e. those reminders for whom the measure of effectiveness may be least accurate).

In the normal mode of operation, the controller 6 can be programmed to select the reminder with the highest measure of effectiveness or a reminder from a set of reminders with the highest measures of effectiveness.

In an alternative embodiment, the controller 6 can operate in a mode that is a hybrid of the normal and training modes. In this mode, the reminder to be used is selected statistically using the measures of the effectiveness and a random contribution. In particular, the higher the measure of effectiveness for a specific reminder (modality and parameter values), the higher the chance of that reminder being used, while the random contribution allows the effectiveness of the other reminders to be evaluated.

An example embodiment can use a probabilistic selection—70% that the measure of effectiveness is used to select the reminder, and 30% that the selection of the reminder is random. The weighted reminder selection could use probabilistic selection where the chance of a reminder, $\text{reminder}_j$, being used is defined by a ratio between the measure of the effectiveness of the reminder, and the sum of the measure of effectiveness for all reminders for which a measure of effectiveness is stored in the memory 10. This is set out in equation (2) below:

$$\text{probability}_{\text{reminder}_j} = \frac{\text{effectiveness}_{\text{reminder}_j}}{\sum_{n=i}^{\text{nr\_reminders\_with\_effectiveness\_measure}} \text{effectiveness}_n} \quad (2)$$

After step 103, the method moves to step 105 in which it is determined whether the user has taken a measurement with the device 2. If the user has not taken a measurement with the device 2, the method waits (in step 107), for example for a few minutes, before moving to step 109.

In step 109, it is determined whether a new reminder should be issued (or whether the previous reminder should be repeated). In this step, the controller 6 can consult the reminder schedule to see if another reminder is scheduled, or the controller 6 can determine if a predetermined period has elapsed since the previous reminder.

If a reminder has just been issued, and/or if the reminder schedule does not indicate that another reminder should be issued, the method returns to step 105.

If another reminder should be issued, the method returns to step 103, and another reminder is issued.

Once the user has taken a measurement (step 105), the method moves to step 111 in which the controller 6 determines the time that has elapsed since the last reminder was issued.

Once this elapsed time has been determined, the controller 6 can update the measure of effectiveness for that reminder using the elapsed time (step 113). The method then returns to step 101 and waits for the next scheduled reminder.

It will be appreciated that the medical monitoring device 2 may also include means for providing the user with a regular or frequent questionnaire or survey that is used to assess the physical or psychological condition or health of the user. In this embodiment, the reminders can be used to prompt the user to complete the questionnaire or survey. In some alternative embodiments, the medical monitoring device 2 may include a questionnaire or survey generating module in place of the physiological characteristic sensor 4.

Figure 3:
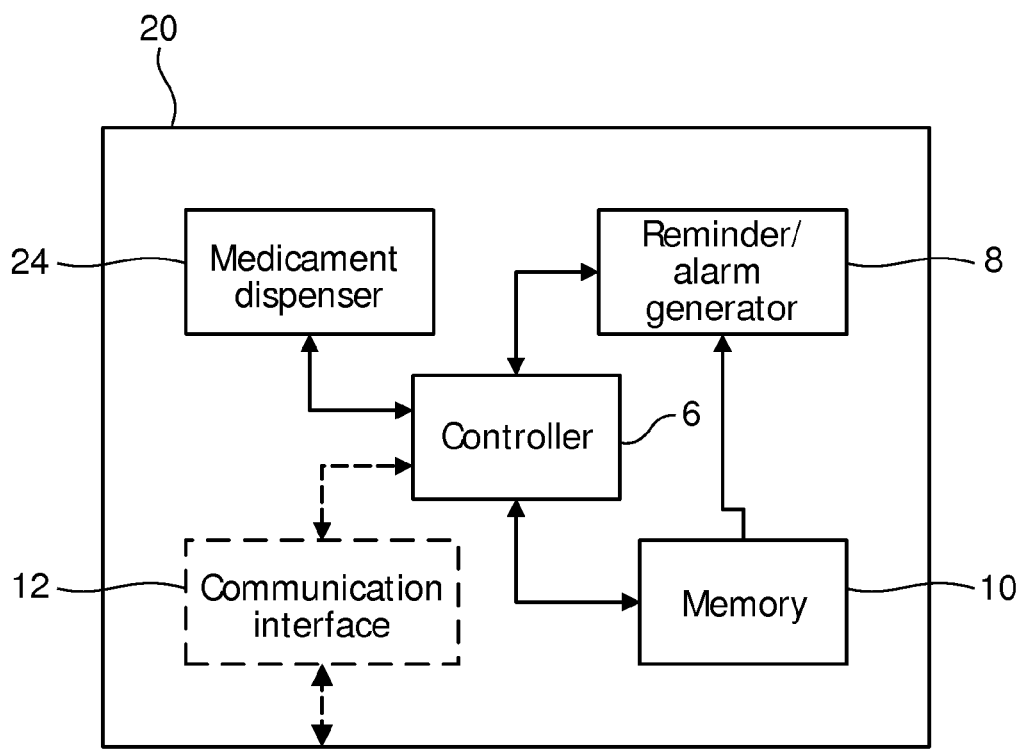
FIG. 3 is a medicament dispensing device according to a second embodiment of the invention.

An alternative embodiment of the invention is shown in FIG. 3, in which the invention is embodied in a medicament dispensing device. The medicament dispensing device 20 in this embodiment has many elements in common with the medical monitoring device shown in FIG. 1, and those common elements have been given the same reference numerals in FIG. 3. These common elements operate in much the same way as those in FIG. 1.

Thus, in this embodiment, the medicament dispensing device 20 comprises a medicament dispenser 24 for storing and dispensing medicaments to the user of the device 20. The reminders issued by the reminder/alarm generator 8 prompt the user to take the medicament from the medicament dispenser 24, and the controller 6 can use the time elapsed from the issue of the reminder to the time that the user took the medicament to update the measure of effectiveness for that reminder.

As described above, in either embodiment, each reminder can have one or more modalities, and has values for various parameters associated with the modalities. Table 1 below illustrates some different parameters for several different types of reminder modality.

TABLE 1

| Reminding modality | Dynamic parameters |
| --- | --- |
| Sound | Volume, tune, delay, frequency |
| Light | Color, intensity, frequency, pattern, delay |
| Scent | Type of scent, intensity |
| Vibration | Power, frequency, delay |
| Spoken message | Message selection, volume, delay |
| Text message | Message selection, delay |
| Video message | Video selection, delay |

In embodiments of the invention, the medical monitoring device or medicament dispensing device comprises various additional features in order to improve the effectiveness of the reminders issued to the user.

For example, if the user does not comply with the required action (i.e. taking a measurement or taking the medicament) and it is necessary to issue a further reminder, the controller 6 may select a reminder that has a higher measure of effectiveness than the previous reminder. In a similar manner, the controller 6 may issue the further reminder with an increased volume or intensity. This can apply equally to reminders that comprise text-based messages, voice messages or video clips, with the content of a subsequent reminder being stronger (i.e. in the sense that the request to comply with the reminder is made more pressing or urgent).

On completion of the required action (i.e. taking a measurement or taking the medicament), the device may provide the user with an acknowledgement message, thanking the user for taking the required action. The device may also, or alternatively, provide the user with statistics relating to their level of compliance with the schedule of required actions.

It may also be possible for the user of the device to provide manual feedback on the effectiveness of the reminders, or the last reminder used, and the controller 6 can use this to update the measure of the effectiveness for those reminders. In this way, the user can be provided with more control over the types of reminders that are issued by the device.

The device can further include a display for indicating the time remaining before the next measurement or medicament needs to be taken by the user (this indicator can itself be considered to be an implementation of a visual reminder).

Although the invention has been described above with reference to a medical monitoring device or a medicament dispensing device, it will be appreciated that a medical device according to the invention can be used to remind the user to carry out various other medical or health related actions, for example taking an insulin injection, using a respiratory drug delivery system, cleaning a wound, using a transcutaneous electrical nerve stimulation (TENS) device, or even brushing teeth.

In yet further embodiments of the invention, the medical device may comprise a module that can be connected to another electronic device, such as a mobile phone, PDA, computer or computer games console. In these embodiments, the module may comprise a controller 6, memory 10 and communication interface 12 as described above (and optionally a sensor 4 or medicament dispenser 24, depending on the specific medical application of the medical device), and the controller 6 in the module can operate to select a reminder to be issued, and can control the electronic device, via the communication interface 12, to issue the reminder to the user.

There is therefore provided a medical device having a reminder function that motivates the patient or user to use the medical device at the appropriate time While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical device having a reminder function, the medical device comprising:

a reminder generator for issuing a reminder to a user to perform a predetermined action with the medical device; and a controller for selecting the reminder from a plurality of available reminders and for controlling the reminder generator to issue the selected reminder in accordance with a reminding schedule;

wherein the controller is configured to maintain a measure of the effectiveness of each of said available reminders and to select the reminder from the plurality of available reminders based on said measures;

wherein the effectiveness of an available reminder is an extent to which the available reminder is successful in achieving user compliance in performing the predetermined action.

2. The medical device as claimed in claim 1, wherein the controller is configured to maintain a measure of effectiveness of each of said available reminders that is based on the average time difference between the issue of said reminder and the user performing the predetermined action.

3. The medical device as claimed in claim 2, wherein, after issue of a reminder, the controller is configured to update the measure of effectiveness for said reminder using $$\text{updated\_effectiveness} = \frac{\text{nr\_times\_used\_before} + 1}{\text{new\_time\_lapse} + \frac{\text{nr\_times\_used\_before}}{\text{previous\_effectiveness}}}$$

where nr_times_used_before is the total number of times that the reminder has been issued, new_time_lapse is the time between the issue of the reminder and the user performing the predetermined action and previous_effectiveness is the value of the measure of the effectiveness for said reminder before said reminder was issued.

4. The medical device as claimed in claim 1, wherein the controller is configured to select the reminder from the plurality of available reminders having the highest measure of effectiveness.

5. The medical device as claimed in claim 1, wherein the controller is configured to select the reminder from a subset of the plurality of available reminders, the reminders in the subset having the highest measures of effectiveness.

6. The medical device as claimed in claim 1, wherein the controller is further configured to operate in a training mode in which the controller selects a reminder from the plurality of available reminders at random.

7. The medical device as claimed in claim 1, wherein the controller is further configured to operate in a training mode in which the controller selects a reminder from the plurality of available reminders that has been used the least times.

8. The medical device as claimed in claim 1, wherein the controller is configured to select the reminder from the plurality of available reminders statistically using the measures of the effectiveness and a random contribution.

9. The medical device as claimed in claim 1, wherein the controller is configured to select the reminder from the plurality of available reminders by using probabilistic selection in which each reminder has an associated probability of selection that is defined by a ratio between the measure of the effectiveness of said reminder and the sum of the measures of effectiveness for each of said reminders in the plurality of available reminders.

10. The medical device as claimed in claim 1, wherein the controller is configured to receive feedback from the user on one or more of the reminders in the plurality of available reminders and to update the measure of the effectiveness for each of said one or more reminders based on said feedback.

11. The medical device as claimed in claim 1, wherein each of the reminders in the plurality of available reminders has one or more modalities selected from sounds, visual elements, vibrations and smells.

12. The medical device as claimed in claim 1, wherein the medical device is a medical monitoring device and further comprises at least one physiological characteristic sensor, wherein the reminder generator is for issuing a reminder to the user to take a measurement using the at least one physiological characteristic sensor.

13. The medical device as claimed in claim 1, wherein the medical device is a medicament dispensing device and further comprises a medicament dispenser, wherein the reminder generator is for issuing a reminder to the user to take a medicament from the medicament dispenser.

14. A method of operating a medical device, the method comprising:

determining that a reminder should be issued to a user of the medical device to remind the user to perform a predetermined action with the medical device;

selecting a reminder from a plurality of available reminders, the selection of the reminder being based on measures of the effectiveness of each of said reminders in the plurality, wherein the effectiveness of an available reminder is an extent to which the available reminder is successful in achieving user compliance in performing the predetermined action; and issuing the selected reminder to the user.

15. The method as claimed in claim 14, further comprising the steps of:

determining the time elapsed from the issue of the selected reminder and the user performing the predetermined action; and updating the measure of the effectiveness of the selected reminder using the determined elapsed time.

16. The non-transitory computer readable medium comprising computer readable code embodied therein, wherein the computer readable code is configured to cause a computer or processor to perform the method of claim 14.

17. A medical reminder device comprising:

a memory configured to store a plurality of reminders to perform a predetermined action and, for each of the reminders, an average time difference between issuing the reminder and a user performing the predetermined action; and a controller configured to:
select one of the reminders stored in the memory based on the stored average time differences;
control a reminder generator to issue the selected reminder;
determine a time difference between issuing the selected reminder and the user performing the predetermined action; and
updating the average time difference for the selected reminder based on the determined time difference.

* * * * *